United States Patent
Seidman

(10) Patent No.: US 7,794,468 B2
(45) Date of Patent: Sep. 14, 2010

(54) MIDDLE EAR RECONSTRUCTION PROCESS AND APPARATUS FOR PERFORMING THE PROCESS

(76) Inventor: Michael D. Seidman, 5310 Putman, West Bloomfield, MI (US) 48323

( * ) Notice: Subject to any disclaimer, the term of this patent is extended or adjusted under 35 U.S.C. 154(b) by 558 days.

(21) Appl. No.: 11/195,460

(22) Filed: Aug. 2, 2005

(65) Prior Publication Data

US 2006/0025754 A1 Feb. 2, 2006

Related U.S. Application Data

(60) Provisional application No. 60/598,191, filed on Aug. 2, 2004.

(51) Int. Cl.
*A61B 18/18* (2006.01)
(52) U.S. Cl. .......................... 606/93; 606/92
(58) Field of Classification Search ............... 606/92, 606/93, 94; 433/80, 81, 89, 90; 604/93.01; 623/10
See application file for complete search history.

(56) References Cited

U.S. PATENT DOCUMENTS

| 4,758,234 | A * | 7/1988 | Orentreich et al. | 604/232 |
|---|---|---|---|---|
| 4,801,263 | A * | 1/1989 | Clark | 433/90 |
| 5,707,584 | A * | 1/1998 | Terpstra et al. | 264/628 |
| 2002/0087164 | A1* | 7/2002 | Speitling | 606/92 |
| 2004/0039244 | A1* | 2/2004 | Kroll et al. | 600/25 |
| 2004/0122377 | A1* | 6/2004 | Fischer et al. | 604/239 |
| 2006/0161255 | A1* | 7/2006 | Zarowski et al. | 623/10 |
| 2006/0178553 | A1* | 8/2006 | Neisz et al. | 600/25 |

OTHER PUBLICATIONS

Kruege et al, Bone Cement Reconstruction of the Ossicular Chain: A Preliminary Report, Jun. 1998, The American Laryngocial, Rhinological & Otalogical Society, Inc., vol. 108(6), pp. 829-836.*
Babu et al, "Ossicular Reconstruction Using Bone Cement," Nov. 2, 2004, Lippincott Williams and Wilkins, pp. 98-101.*

(Continued)

*Primary Examiner*—Eduardo C Robert
*Assistant Examiner*—Jan Christopher Merene
(74) *Attorney, Agent, or Firm*—Gifford, Krass, Sprinkle, Anderson & Citkowski, P.C.

(57) ABSTRACT

Erosion of elements of the ossicular chain in the middle ear, resulting in hearing loss, is corrected by creating a bridge between the eroded elements, employing a bone cement formed as a paste of a self-hardening material, which is molded into an elongated bridge, secured at its two ends to the elements to be bridged, and supported in its desired position until the material hardens to fuse the two elements, at which time the support may be removed. The material is preferably hydroxyapatite cement, bone source, or similar material, such as ionomeric bone cement. These materials strongly bond to the contacting bone and may stimulate bone in-growth, resulting in osseointegration. The apparatus for forming the bridge consists of a reservoir of the bridge material in liquid or paste form connected to a bridge supporting tube. The tube is preferably placed in contact with the two elements to be bridged and the bone source material is injected into the tube using a manually actuated plunger until the tube is full. The tube is then supported, manually or otherwise, until the material hardens and the supporting tube is removed.

8 Claims, 4 Drawing Sheets

OTHER PUBLICATIONS

Seilesh Babu and Michael D. Seidman; Ossicular Reconstruction Using Bone Cement;Otology and Newrotology, vol. 25, No. 2, 2004, pp. 98-101.
W. Lorenz Surgical, A Biomet Company, Bridge the Gap Mimix Bone Replacement System, ; 2 pages.
Carolyn Waddington, Ann T. McKennis; Treatment of Conductive Hearing Loss With Ossicular Chain Reconstruction Procedures-Otorhinolaryngology Surgery Update; Mar. 1997; 4 pages.
The Encyclopaedia of Medical Imaging, vol. VI 2; Ossicular Chain;3 pages, Published Apr. 19, 2002.

* cited by examiner

MIDDLE EAR RECONSTRUCTION PROCESS AND APPARATUS FOR PERFORMING THE PROCESS

RELATED APPLICATION

This application claims priority of U.S. Provisional Patent Application Ser. No. 60/598,191 filed Aug. 2, 2004, which is incorporated herein by reference.

FIELD OF THE INVENTION

This invention relates to methods and apparatus for repairing discontinuities of elements of the ossicular chain in the middle ear resulting from erosion and the like and more particularly to a process and apparatus for creating a bridge between the eroded elements employing a bone cement.

BACKGROUND OF THE INVENTION

Sound conduction in the ear requires an intact ossicular chain (the bones in the middle ear). Because of chronic infection, trauma or cholesteatoma (skin in the middle ear) the ossicular chain may become eroded. This causes a 20-55 decibel conductive hearing loss.

The normal ossicular chain functions as an efficient lever system that transfers sound from the tympanic membrane to cochlear fluids. Interruption of the ossicular chain can be caused by erosion, most commonly at the long process or lenticular process of the incus.

Previous methods of repairing such discontinuities primarily involved the implantation of prosthetic elements. A wide variety of forms of implants must be made available. It has proven difficult to accurately position the implants which often slip, become dislodged or extrude through the eardrum. Success of the implants, in terms of closing the air-bone gap so as to provide effective hearing, is limited. It has alternatively been proposed to manually form a linking section out of a bone cement or other self-hardening material and using it to bridge the disruption in the ossicular chain.

SUMMARY OF THE INVENTION

The present invention is directed toward a method of repairing discontinuity of elements of the ossicular chain by bridging the discontinuity with an elongated fusing strip formed out of a paste of bone material and more particularly creating the fusing link out of a manually moldable paste of a self-hardening material, disposing the fusing strip on an elongated bridge-supporting tube and maintaining the support provided by the tube while the paste hardens to a self-supporting condition. The tube may then be removed or, alternatively, elements of the tube which are inert may be maintained on the fusing link.

The material used to form the link is preferably hydroxyapatite cement, bone source, ionomeric bone cement or similar material. These materials strongly bond to the contacting bone and may stimulate bone in-growth, resulting in osseointegration.

The apparatus for forming the bridge consists of a bridge-supporting tube, which may be of adjustable length, which is disposed between the two ends of the elements to be bridged. The bone source paste may be manually inserted onto the bridging tube or it may be injected from a syringe having its output connected to the tube. The tube is then supported manually, by a handle extending normally to the tube, or otherwise, until the material hardens and the supporting tube may be removed.

In one embodiment of the invention the supporting tube includes a sleeve formed of silicone film or the like which may remain in place on the hardened tube.

BRIEF DESCRIPTION OF THE DRAWINGS

Other objects, applications and advantages of the present invention will be made apparent by the following detailed description of a preferred embodiment of the invention. The description makes reference to the accompanying drawings in which.

DETAILED DESCRIPTION OF THE INVENTION

Figure 1:
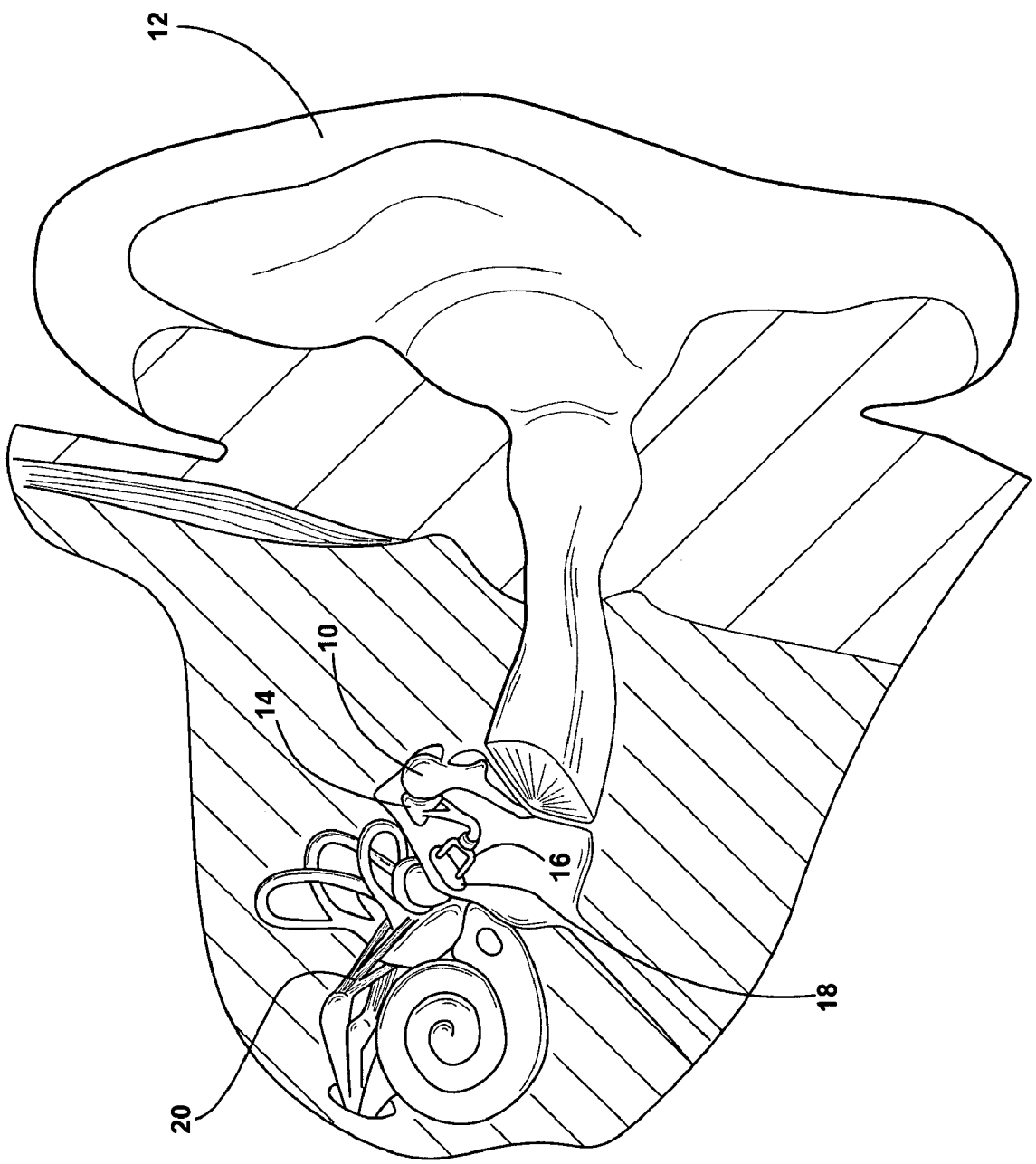
FIG. 1 is a sectional view through a normal right ear illustrating an intact ossicular chain.

The fusing links formed by the method and apparatus of the present invention may be broadly classified as bone paste. Preferably, these bone cements employ calcium phosphate based materials. Hydroxyapatite (HA) is a type of calcium phosphate material that is a major inorganic constituent of bones. Corals create a calcium carbonate exoskeleton resembling human bone with an average pore size of 200 microns. This exoskeleton is then converted into HA through an exchange reaction of the carbonate for phosphate. The resultant material has the porous anatomy of bone with identical chemical composition. HA is capable of strongly bonding to adjacent bone and stimulating bone in-growth resulting in osseointegration. It does not elicit a foreign body or immunological response.

Another type of bone cement, Oto-Cem or CrenoCem, is an ionomeric bone cement. Clinical reports show promising results using Oto-Cem in closure of the air-bone gap in patients with incus necrosis. They also show use of bone cement in reconstructing other defects of the ossicles with adequate results. Ionomeric bone cement is a hybrid composite material consisting of inorganic aluminum fluorosilicate particles in a hydrogel matrix. Ionomeric bone cement must be used with great caution around neural tissue with a serious risk of aluminum toxicity. Also, side-effects such as granular formation or reaction to the cement have been described.

HA cement is self-hardening and forms pure hydroxyapatite when set. This material has been used successfully in many craniofacial applications. Hydroxyapatite and HA cement are biocompatible and do not elicit a foreign body reaction. When mixed with water, hydroxyapatite cement (HAC) forms a paste that may be manipulated and shaped which then hardens within 15-30 minutes, achieving a self-supporting rigidity in a substantially shorter time. By mixing HAC with a solution of sodium phosphate concentration of approximately 0.25 mol/L, the setting times can be reduced to 5-8 minutes, the time required for self-supporting rigidity reduced commensurately, and the tensile strength increased in the first 3 hours.

Advantages of using bone cement include the maintenance of normal anatomy, ease of use, closure of air-bone gap, and cost effectiveness. The incus does not need to be removed in cases of limited incus necrosis and may be reconstructed using this technique. Leaving normal anatomy in place in the middle ear is likely to be beneficial for sound conduction. Studies have determined that the stiffness of the prosthesis has a significant effect on vibratory coupling between the tympanic membrane and the stapes. The middle ear prosthesis should ideally match the impedance or stiffness of the natural ossicular system. The conclusion is that the prosthesis should be as light as possible but sufficiently rigid to transport vibration. HAC is both light and provides rigidity for sound conduction. Leaving the incus in place and using HAC should provide vibratory transmission of sound with excellent impedance matching.

FIG. 1 illustrates a cross section through a normal right ear 12, with the top of the head to the left. This figure shows the malleus 10, the incus 14 and the stapes 16 intact about an integral stapes footplate 18. The facial nerve 20 transmits impulses generated by vibration of the eardrum through the ossicular chain to nerves which generate electrical signals for the brain.

Figure 2:
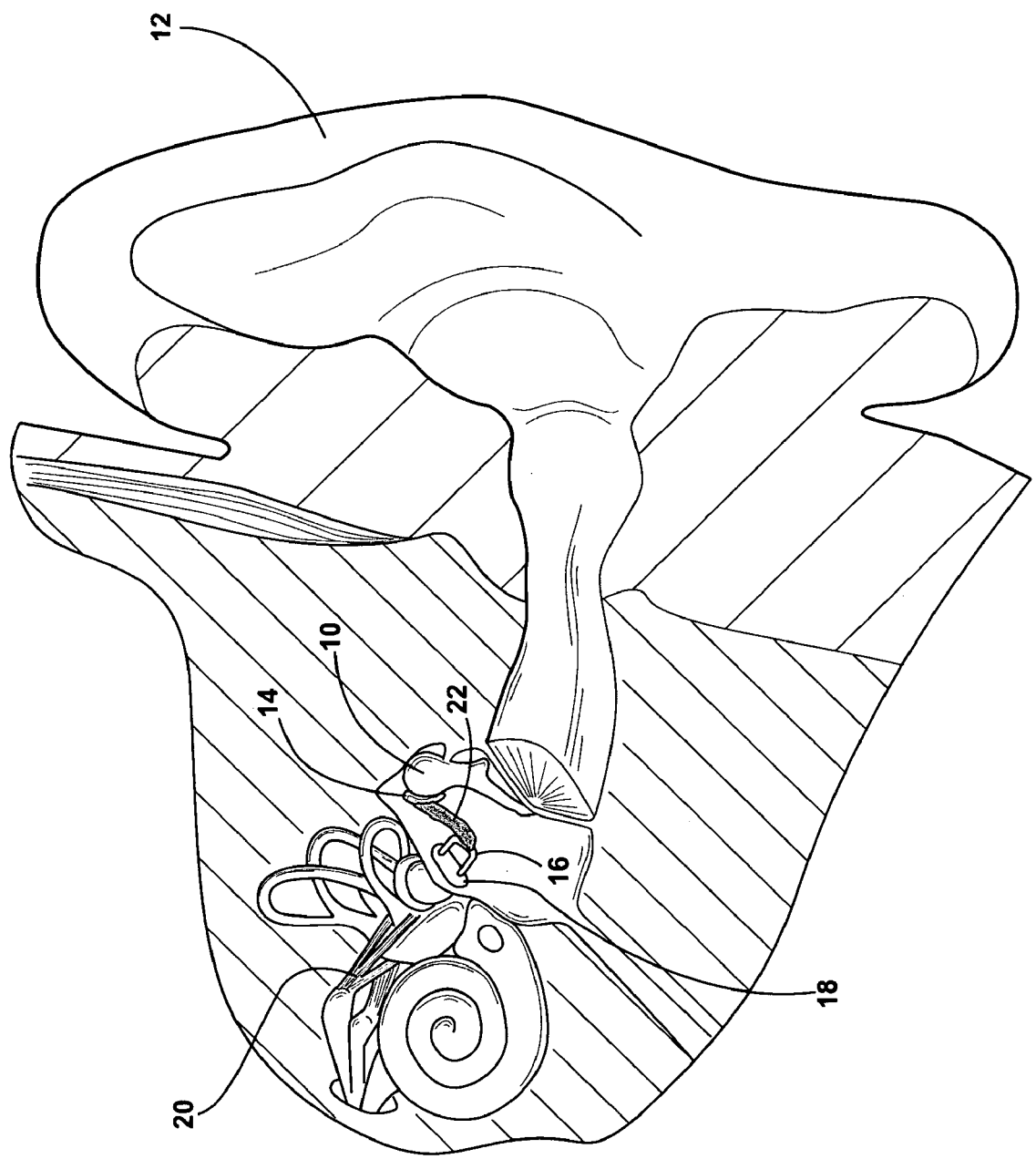
FIG. 2 is an illustration similar to FIG. 1 illustrating an ossicular chain in which the incus is eroded and illustrating a fusing element joining the incus and the stapes, which is formed in accordance with the present invention.

FIG. 2 shows the same structure with the incus eroded and a fusing link 22 of bone cement extending between the eroded section of the incus and the stapes. Link 22 restores normal hearing function and is formed in accordance with the present invention, preferably using instruments to be subsequently described.

Figure 3:
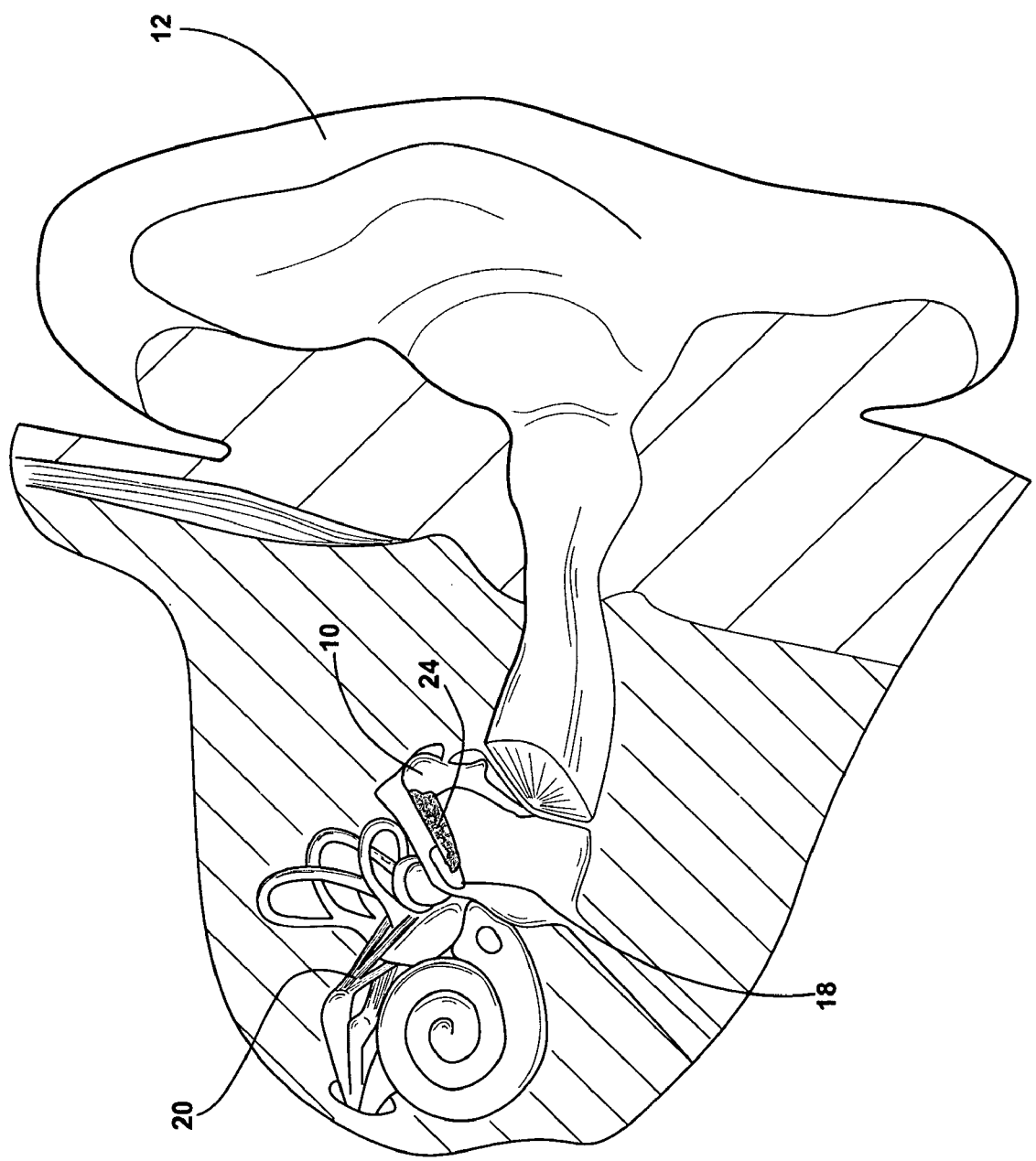
FIG. 3 is an illustration similar to FIG. 1 illustrating the ossicular chain in an ear in which both the incus and the superstructure of the stapes have been eroded, leaving only the footplate of the stapes, with a fusing link joining the malleus to the footprint of the stapes, formed in accordance with the present invention.

FIG. 3 is a similar illustration of the inner ear with the incus fully eroded and the superstructure of the stapes eroded, leaving only the footplate 18. A fusing link of bone cement 24 is established between the malleus and the footplate of the stapes restoring hearing.

Fusing links of this type provided an air-bone gap closure within 20 dB in 94.4% of patients with at least a 12 month postoperative follow up in a study of 18 patients which I conducted. One patient had a reduction of their air-bone gap from 53 dB to 24 dB and was not counted as a successful closure. The distance of the necrosis in this patient was 3 mm. There was a closure within 10 dB in 70% of the 18 patients in the study. These results are promising and provide a safe, stable alternative to reconstructing the ossicular chain without removal of the incus and provide excellent postoperative hearing.

Figure 4:
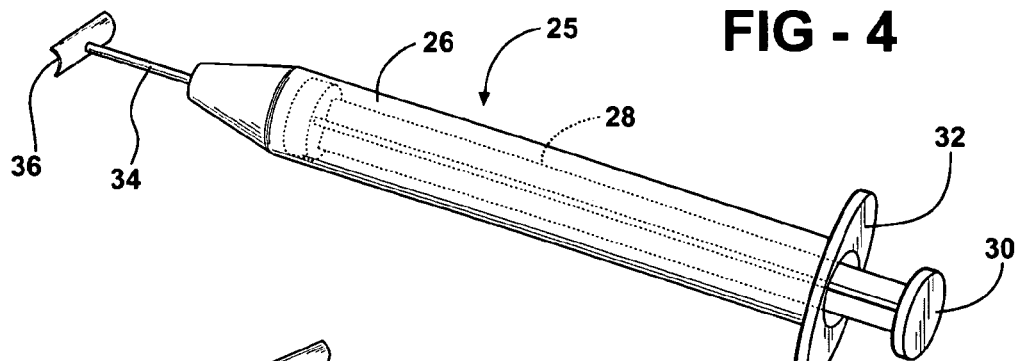
FIG. 4 illustrates an apparatus for creating and supporting a fusing link.

FIG. 4 illustrates an instrument, generally indicated at 25, for creating a fusing link of the type illustrated in 22 and 24 of FIGS. 2 and 3 respectively, bringing the opposite ends of the link into contact with the two points in the ossicular chain to be joined, and supporting the link for a sufficient period of time to allow it to become self-supporting. The instrument 25 constitutes a syringe body 26 having a plunger or piston 28 movable through the body based on forces applied to an end 30. The body 26 includes a flange 32 and forces exerted between the end 30 and the flange 32 can force material through the body. The distal end of the body connects to a small diameter tube 34 which supports a fusing link trough 36 on its far end.

The syringe body 26 is filled with a volume of an HAC paste formed in accordance with the present invention. When force is applied to the end of the piston 28, it forces bone material out the tube 34 which connects to the center of the trough 36. The bone material may be manually spread along the length of the trough 36 to a desired length. The ends of the paste link thus formed are brought into contact with the two points of the ossicular chain which are to be joined and the instrument 25 is supported, manually or otherwise, for a sufficient period of time to allow the link to harden to a self-supporting state. The instrument is then removed. The bottom of the trough 36 may be coated with a silicone to assist in removal.

Figure 5:
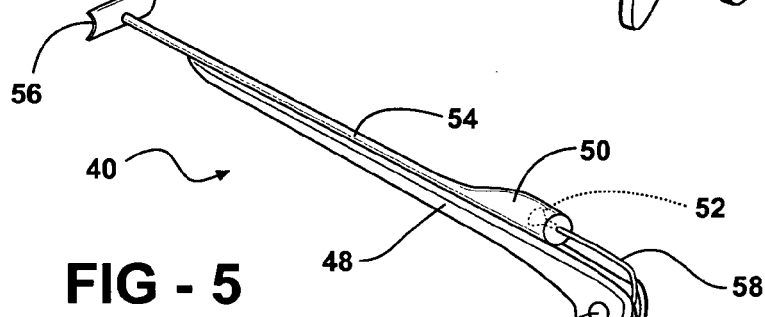
FIG. 5 illustrates an alternative form of apparatus for creating and supporting a fusing link.

An alternative type of instrument, formed in accordance with the present invention, for the practice of the present method, is generally indicated at 40 in FIG. 5. It constitutes a forceps-type instrument comprising a pair of handles 42 and 44 pivotally supported to a body about a pin 46. The body extends in elongated fashion at 48. A cylinder 50 adapted to be filled with a bone cement of the type used in connection with the present invention is supported on the extension 48. The piston 52 which fits within the syringe 50 is connected by a cable 54 to the pivotal handle 44 in such a way that when the handles 42 and 44 are forced together, the bone source paste filling the syringe 50 is forced up a narrow tube 54 to support tube 56 extending beyond the projection 48. Again, the paste passes from the line 54 into the tube 56 where it may be manually molded to a desired length and brought into contact with the interrupted points in the ossicular chain. The instrument 40 then supports the bridging element until it is self-hardening.

Figure 6:
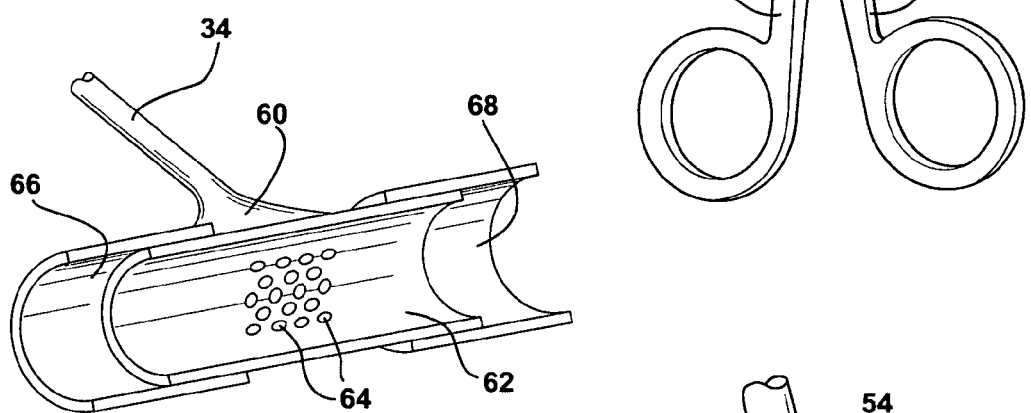
FIG. 6 is a perspective drawing of a link supporting tube useful with the devices of FIG. 4 or 5.

A detailed view of the support structure for a fusing link which may be incorporated in either of the instruments of FIG. 4 or 5 or other like instruments is illustrated in FIG. 6. The link support consists of an elongated semi-tubular section 62 having a plurality of holes 64 in the center of the section. The holes 64 connect to a manifold 60 which receives bone cement paste from the tube 34 of the instrument 25 of FIG. 4 or the tube 54 of the device 40 of FIG. 5. The paste then flows through the holes 64 into the concave side of the tube section 62 where it may be manually manipulated to the proper form. The tube section 62 has a pair of concentric semi-tubular wings 66 and 68 adjustably supported on either of its ends. These wings may be used as extensions and may be adjusted to achieve the proper length of support for the bone paste.

Figure 7:
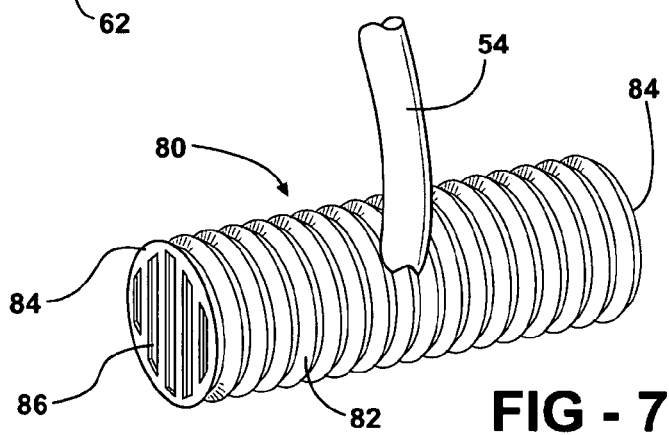
FIG. 7 is a detailed perspective view of the alternative form of link supporting tube.

FIG. 7 illustrates an alternative form of a support for the bone paste which may be used with either of the instruments of FIG. 4 or 5. The conduit 54 for bone paste feeds through the exterior wall of a corrugated, accordion-like support, generally indicated at 80. The device 80 includes a corrugated accordion-like elongated tube 82 formed of a plastic film which is inert and may be left in place following the procedure. The accordion tube 82 has end sections 84 formed with slits 86. The section 82 is placed between the two sections of the ossicular chain which are to be joined and HAC paste is forced through the tube 54, filling and expanding the tube 82 into the appropriate length, until the bone paste begins to ooze out of the slits 86 in the ends of the tube 82 against the chain sections to be joined. The tube is then manually supported until the section is sufficiently hardened to be self-supported and then the tube 54 is removed, leaving the film section 82 in place. The material which seeps out of the ends forms a continuous sound-conducting element between the two points in the ossicular chain requiring connection.

Having thus described my invention, I claim:

1. A method for repairing an ossicular discontinuity, comprising the steps of:

forming an elongated fusing strip out of a paste of bone material on a manually supported fuser support having an elongated handle and an elongated fuser support member connected to one end of the handle and extending substantially perpendicular to the handle, the support leaving both ends of the strip exposed, the ends of the strip defining the length of said strip, which is greater than the width of said strip;

manipulating the fuser support to simultaneously bring both ends of said strip into contact with the two ossicular elements forming the discontinuity in the ossicular chain;

continuing to support the fuser support with the ends of the strip in contact with the two ossicular elements while the strip hardens to self-supporting condition; and removing the fuser support.

2. The method of claim 1 wherein the fusing strip is formed of hydroxyapatite.

3. The method of claim 1 wherein the fusing strip is formed of an ionomeric bone cement.

4. The method of claim 1 wherein the fusing strip is formed of inorganic aluminum fluorosilicate particles in a hydrogel matrix.

5. The method of claim 1 wherein the elongate fuser support member is semi-circular in configuration.

6. The method of claim 1 wherein the elongate fuser support member constitutes the interior of a tube.

7. The method of claim 1 wherein the bone cement is fed onto the support from a syringe forming part of said elongated handle.

8. The method of claim 7 wherein the syringe includes a manually actuated plunger for pressurizing the bone cement and forcing it onto the fuser support.

* * * * *